United States Patent
Hofmann (10) Patent No.: US 7,578,174 B2
(45) Date of Patent: Aug. 25, 2009

(54) APPARATUS FOR ANALYZING A LIQUID SAMPLE USING A MULTIPLE-LUMEN CAPILLARY

(75) Inventor: Martin Hofmann, Rheinstetten (DE)

(73) Assignee: Bruker Biospin GmbH, Rheinstetten (DE)

( * ) Notice: Subject to any disclaimer, the term of this patent is extended or adjusted under 35 U.S.C. 154(b) by 113 days.

(21) Appl. No.: 11/798,345

(22) Filed: May 14, 2007

(65) Prior Publication Data

US 2007/0266779 A1  Nov. 22, 2007

(30) Foreign Application Priority Data

May 18, 2006  (DE)  ........................ 10 2006 023 223

(51) Int. Cl.
*G01N 1/00* (2006.01)
(52) U.S. Cl. .................................. 73/64.56; 73/863.31
(58) Field of Classification Search ................ 73/64.56, 73/863.31, 863.32, 863.33
See application file for complete search history.

(56) References Cited

U.S. PATENT DOCUMENTS

| | | | | |
|---|---|---|---|---|
| 3,570,673 | A * | 3/1971 | Dutz et al. ............... | 210/198.2 |
| 4,424,127 | A * | 1/1984 | Roeraade ................. | 210/198.2 |
| 4,818,264 | A * | 4/1989 | Langhorst ................ | 65/439 |
| 5,764,356 | A | 6/1998 | Iwase | |
| 6,174,352 | B1 * | 1/2001 | Semerdjian et al. ....... | 96/8 |
| 6,270,674 | B1 * | 8/2001 | Baurmeister et al. ...... | 210/649 |
| 6,383,452 | B1 | 5/2002 | Miyake | |
| 6,387,234 | B1 * | 5/2002 | Yeung et al. ............. | 204/451 |
| 6,462,546 | B1 | 10/2002 | Schmalbein | |
| 6,783,650 | B2 * | 8/2004 | Hayashizaki et al. ...... | 204/603 |
| 7,166,212 | B2 * | 1/2007 | Belov et al. ............. | 210/198.2 |
| 7,214,320 | B1 * | 5/2007 | Gregori et al. ........... | 210/656 |
| 7,261,812 | B1 * | 8/2007 | Karp et al. .............. | 210/198.2 |
| 7,273,517 | B1 * | 9/2007 | Lewis et al. ............. | 96/101 |
| 7,419,830 | B2 * | 9/2008 | Canos et al. ............ | 436/37 |
| 2002/0166367 | A1 * | 11/2002 | Bures .................... | 73/54.04 |
| 2003/0082081 | A1 | 5/2003 | Fouillet | |
| 2005/0031491 | A1 * | 2/2005 | Corma Canos et al. ..... | 422/68.1 |
| 2005/0100476 | A1 | 5/2005 | De Mello | |
| 2005/0280416 | A1 | 12/2005 | Hofmann | |
| 2006/0094119 | A1 | 5/2006 | Ismagilov | |

FOREIGN PATENT DOCUMENTS

| | | |
|---|---|---|
| DE | 693 03 483 | 2/1997 |
| DE | 693 19 427 | 12/1998 |
| DE | 198 46 466 | 4/2000 |
| DE | 102 28 089 | 1/2004 |
| DE | 102 44 154 | 4/2004 |

(Continued)

*Primary Examiner*—John Fitzgerald
(74) *Attorney, Agent, or Firm*—Paul Vincent (57) ABSTRACT

An apparatus for analyzing a measuring substance which is dissolved in a solvent, comprising a conduit (4) for transporting the dissolved measuring substance from a feed means (3) to a measuring location (12), wherein the feed means (3) is designed to optionally feed a solvent or dissolved measuring substance into the conduit (4), is characterized in that the conduit (4) is designed, at least partially, as a polycapillary area (9) which has N parallel connected capillaries (21a, 21b, 21c; 62a, 62b), such that the individual capillaries (21a, 21b, 21c; 62a, 62b) have identical flow times from the feed means (3) to the measuring location (12) and wherein $N \geq 2$. The apparatus improves the signal-to-noise ratio of the analysis.

14 Claims, 6 Drawing Sheets

FOREIGN PATENT DOCUMENTS

| | | |
|---|---|---|
| DE | 10 339 452 | 3/2005 |
| EP | 0 803 288 | 10/1997 |
| GB | 1 186 197 | 4/1970 |
| WO | WO 02/50535 | 6/2002 |
| WO | WO 03/098218 | 11/2003 |
| WO | WO 2005/090970 | 9/2005 |

* cited by examiner

APPARATUS FOR ANALYZING A LIQUID SAMPLE USING A MULTIPLE-LUMEN CAPILLARY

This application claims Paris Convention priority of DE 10 2006 023 223.2 filed May 18, 2006 the complete disclosure of which is hereby incorporated by reference.

BACKGROUND OF THE INVENTION

The invention concerns an apparatus for analyzing a measuring substance which is dissolved in a solvent, comprising a conduit for transporting the dissolved measuring substance from a feed means to a measuring location, wherein the feed means is designed to optionally feed a solvent or a dissolved measuring substance into the conduit.

An apparatus of this type is disclosed in DE 10 2004 029 632.

LC-NMR (hyphenated liquid chromatography nuclear magnetic resonance) or FI-NMR (flow injection nuclear magnetic resonance) can be used to analyse soluble substances. A liquid sample (generally a mixture of a solvent and the substance to be measured) is thereby guided from a feed means through a conduit, in particular, a glass or plastic capillary, to a measuring location in an NMR spectrometer.

The liquid sample is thereby typically pushed by subsequently fed transport solvent and the liquid sample is, in turn, pushed by the transport solvent. A so-called "plug flow" is thereby desired, i.e. the liquid sample moves through the conduit like a plug with flat interfaces relative to the transport solvent which extend perpendicularly to the transport direction.

When the liquid sample advances through the conduit, the sample is spread. The speed of laminar flow is maximum in the center of a capillary and drops off towards the edges, approximately like a parabola. The sample front then assumes an approximately parabolic cross-sectional shape.

When the sample advances, the liquid sample is consequently distributed over an extending section of the capillary, i.e. the concentration of substance to be measured in the conduit decreases. This decreased concentration of substance to be measured deteriorates the signal-to-noise ratio (SNR) of the NMR measurement at the measuring location.

Similar problems also occur in other measuring methods using liquid samples, such as UV (ultra violet) absorption or UV fluorescence.

The "Nanotight Y Connector" by Upchurch Scientific Inc., Catalog of Chromatography & Fluid Transfer Components 2006, page 39, discloses a distributor element for splitting a sample flow from a large capillary into two individual capillaries. This distributor element is used to distribute a liquid sample to two measuring means to which the individual capillaries are guided.

It is the underlying purpose of the present invention to provide an apparatus for analyzing a measuring substance which is dissolved in a solvent, wherein the apparatus improves the signal-to-noise ratio of the analysis.

SUMMARY OF THE INVENTION

This object is achieved by an apparatus of the above-mentioned type which is characterized in that the conduit is at least partially designed as a polycapillary area which has N parallel connected capillaries, such that the individual capillaries have identical flow times from the feed means to the measuring location, wherein $N \geq 2$.

The flow profile in a capillary depends on the inner diameter (ID) of the capillary. At identical average flow speeds (transported liquid volume per cross-sectional area and unit time), a sample in a capillary with a smaller diameter is spread less than in a capillary with a larger diameter. Thus, by using a capillary with small diameter, the sample smears less. However, a smaller diameter also reduces the overall liquid sample flow. The conduit resistance of the capillary is also increased which must be compensated for by increasing the pressure.

In accordance with the invention, the desired overall liquid sample flow is therefore distributed over several capillaries which extend parallel to each other. Each individual capillary has a relatively small inner diameter in the polycapillary area compared to the inner diameter of an equivalent capillary whose cross-sectional area is equal to the sum of the cross-sectional areas of the individual capillaries of the polycapillary area. The liquid sample is smeared less during transport through the conduit in each individual capillary and therefore also over the entire conduit.

The individual capillaries are designed such that when a sample is fed into the polycapillary area, the sample fronts in each individual capillary require the same time to pass through the polycapillary area. The front tips of the sample fronts may thereby be e.g. compared. In the simplest case, the individual capillaries therefore have identical design, in particular the same length, the same inner diameter, and the same inner surface.

The liquid sample is distributed to the individual capillaries at the entry of the polycapillary area, and the liquid sample is reunited at the end of the polycapillary area with little smearing and typically directly before the measuring location. A conduit in accordance with the invention may comprise one polycapillary area or several polycapillary areas which are disposed consecutively in series.

Cleaning of the inventive apparatus is also accelerated due to reduced smearing, requiring less cleaning and rinsing liquid.

When, in an existing apparatus, one single large capillary of one conduit is to be replaced by a polycapillary area, the sum of the cross-sectional areas of the individual capillaries of the polycapillary area should correspond to the cross-sectional area of the large capillary. Retrofitting of existing apparatus can thereby be easily realized. Four individual capillaries with an inner diameter of 250 μm correspond e.g. to a large capillary of a diameter of 500 μm.

In one particularly preferred embodiment of the inventive apparatus, the individual capillaries have identical inner diameters and identical lengths. Moreover, the individual capillaries preferably also have identical inner surfaces, e.g. an identical inner coating or the same capillary material. The inner diameter and the inner surface determine the flow profile or the flow speed in the capillary. Identical flow speeds and identical lengths produce identical flow times of the liquid sample. This embodiment easily realizes identical flow times for a liquid sample in the individual capillaries. Quartz glass capillaries maintain particularly narrow inner diameter (and outer diameter) tolerances.

In an alternative embodiment, the length of one single capillary is adjusted to the flow speed in this capillary. Due to production tolerances, e.g. of the inner diameter, the flow speeds in the individual capillaries of a polycapillary area may slightly differ. This can be easily determined through previous measurement of the individual capillaries. In accordance with the invention, the individual capillary with the highest flow speed is e.g. left unchanged and the individual capillaries with a smaller flow speed are shortened in correspondence with their deviation. This also ensures identical flow times through all individual capillaries of the polycapillary area. The flow speed can be measured e.g. using the advance of the tip of a sample front.

In another preferred embodiment, the overall conduit is designed as a polycapillary area. Spreading of the sample is reduced to a maximum extent. Further components such as a chromatography column may be contained in the conduit, which are each connected to polycapillary areas.

In a preferred embodiment, the conduit contains a chromatography column. The chromatography column separates different components of a sample.

In another preferred embodiment, the conduit terminates in a measuring cell at the measuring location. The measuring cell is one single chamber, wherein the actual analysis measurement of liquid sample takes place in the chamber. The measuring cell, in particular its dimensions, is adjusted to analysis measurement.

In an alternative embodiment, the measuring location may be designed as a polycapillary area. The capillaries have very thin walls compared to typical measuring cells (capillaries typically 70 to 170 µm, measuring cells 150 to 500 µm). Absorption losses can thereby be reduced, in particular, in NMR measurements.

In one particularly preferred embodiment, the capillaries have a hydrophobic inner coating. The hydrophobic (non-polar) inner coating, e.g. of FEP, improves the flow profile, in particular, when polar (transport) solvents such as water are used. A liquid sample will then spread less than without a hydrophobic inner coating, i.e. the parabolic flow profile is flatter. A coating also means surface treatment (passivation) of the inner surface. This has proven to be advantageous for quartz glass capillaries. An inventive non-polar capillary inner surface may also be obtained by a non-polar base material of the capillary itself.

In another preferred embodiment, the number N of capillaries in the polycapillary range is between 2 and 7. This number is easy to handle, in particular, simultaneous supply of the individual capillaries with liquid sample is still easily possible.

One embodiment has proven to be useful in practice, with which the inner diameter of the capillaries is between 50 µm and 500 µm. This realizes good flow performance without excessively increasing the transport pressure or excessively spreading the sample.

One advantageous embodiment comprises a plastic coating in which the capillaries extend. The plastic coating protects the capillaries of the polycapillary area from damage.

In another preferred embodiment, the capillaries are individually guided in some areas through bores of guiding elements. The guiding elements may e.g. be inserted at the start and end of a polycapillary area, i.e. as a part of a distributor element. The guiding elements can preferably be elastically deformed. Slight compression seals the bores from the capillaries and the individual capillaries can be held. The capillaries may be slightly shifted within the bores for adjustment, if required.

In another preferred embodiment, the inlet of the polycapillary area has a distributor element for the N capillaries. Typically, a large capillary leads to the distributor element, and opens in a widening distributor chamber. The individual capillaries of a polycapillary area exit opposite to the opening of the large capillary. The distributor chamber is preferably sufficiently small (e.g. $\leq 20$ nL volume) such that the flow paths within the distributor chamber are small compared to flow paths within the individual capillaries of the polycapillary area.

In a further development of this embodiment, the N capillaries are disposed symmetrically about a central axis in the distributor element and at identical separations from the central axis. A large capillary preferably terminates on the central axis opposite to the individual capillaries. The symmetry ensures simultaneous feeding of the individual capillaries of the polycapillary area.

In one particularly preferred embodiment, the apparatus is designed as an NMR spectrometer or UV detection apparatus. These sensitive methods profit especially from a higher measuring substance concentration in the analysis.

Further advantages of the invention can be extracted from the description and the drawing. The features mentioned above and below may be used in accordance with the invention either individually or collectively in arbitrary combination. The embodiments shown and described are not to be understood as exhaustive enumeration but have exemplary character for describing the invention.

The invention is shown in the drawing and explained in more detail with reference to embodiments.

BRIEF DESCRIPTION OF THE DRAWING

FIG. 6b shows a schematic view of the flow profiles of two capillaries with the same total overall cross-sectional area as the large capillary of FIG. 6a;

DESCRIPTION OF THE PREFERRED EMBODIMENT

Figure 1:
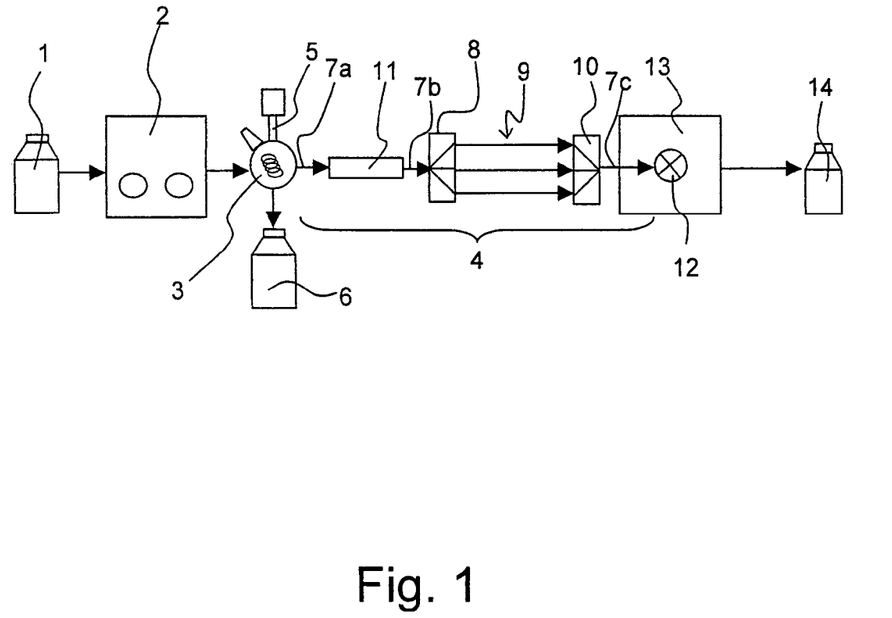
FIG. 1 shows an inventive apparatus with a conduit having a polycapillary area.

FIG. 1 schematically shows the structure of an inventive apparatus for investigating a measuring substance dissolved in a solvent, using instrumental analysis, in particular using NMR spectrometry.

Transport solvent is supplied from a supply container 1 for a transport solvent or mobile liquid, using a pump 2, to a feed means (or injector) 3. The transport solvent is either directly supplied through the feed means 3 into a line 4 or via a sample storage in the feed means 3. In the latter case, the content of the sample storage, which is pushed by the transport solvent, is supplied to the conduit 4. The sample storage can be filled with a liquid sample via an injection connection 5. The liquid sample comprises a solvent which contains the dissolved substance to be measured (measuring substance). Excessive amounts of sample can be discharged into a waste container 6.

The conduit 4 is designed as a large capillary in a first short transition section 7a directly behind the feed means 3. The first transition section 7a terminates in a chromatography column 11. The supplied liquid is further supplied to a distributor element 8 via a second transition section 7b. The conduit 4 extends from the distributor element 8 in the form of a polycapillary area 9 with several (in the present case three) individual capillaries, in which the supplied liquid is propagated in parallel. The flows of the individual capillaries are united at a unification element 10 which has a similar structure as the distributor element 8, and are transferred to a third transition section 7c.

The supplied liquid is supplied to a measuring location 12 via the third transition section 7c. The measuring location 12 is disposed in a detector 13, in the present case an NMR spectrometer. The actual analytical measurement takes place at the measuring location 12. The supplied liquid is finally disposed into a waste container 14.

The conduit 4 connects the feed means 3 to the measuring location 12 of the apparatus. The major part of the conduit 4 thereby extends as a polycapillary area 9 to reduce spreading of the liquid sample during transport.

Figure 2:
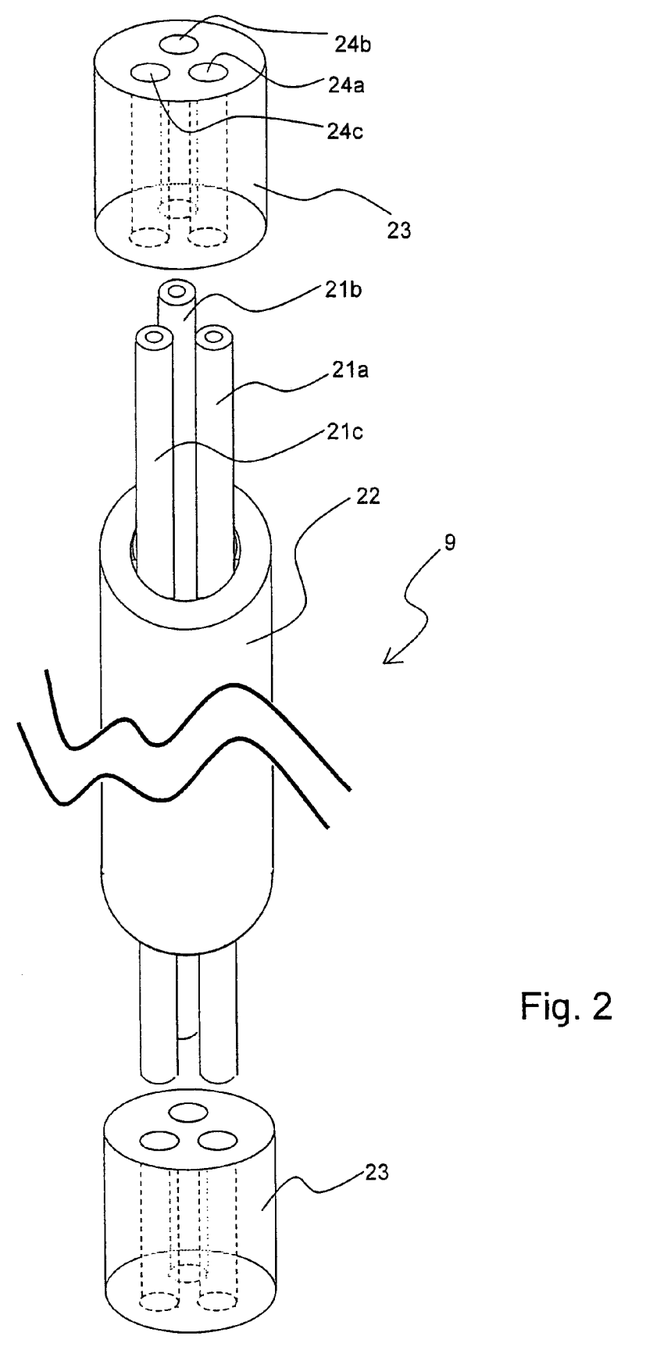
FIG. 2 shows a schematic perspective exploded view of a polycapillary area of a conduit as used in accordance with the invention.

FIG. 2 shows an exploded schematic view of a polycapillary area 9. The polycapillary area 9 comprises three individual capillaries 21a, 21b, 21c, which are produced from fused silica. The capillaries 21a-21c have an outer plastic coating, e.g. of PEEK (polyether ether ketone) (not shown) in order to guarantee the flexibility of the capillaries 21a-21c. The inner surfaces of the capillaries 21a-21c are coated with a hydrophobic substance, e.g. FEP (tetrafluoroethylene perfluoropropylene) (not shown). All capillaries 21a-21c have identical lengths, identical inner diameters and identical outer diameters. The production tolerance of the capillaries relative to the inner diameters is +/−2% or less over the entire length, the maximum length difference between the capillaries should be at most +/−1%.

The three capillaries 21a to 21c are disposed in a flexible plastic coating 22. This reduces the mechanical load on a comparably sensitive individual capillary 21a, 21b, 21c in handling the polycapillary area 9 (e.g. when the conduit is laid). Illustration of the plastic coating 22 is interrupted for simplification. The plastic coating 22 is slightly shorter than the capillaries 21a-21c.

Circular cylindrical, elastically deformable guiding elements 23 are provided at the upper and lower ends of the polycapillary region 9. Three bores 24a, 24b, 24c are provided in the guiding elements 23, whose bore diameters are slightly larger than the outer diameters of the capillaries 21a-21c (e.g. with a bore diameter 370 µm and outer diameter of the capillaries 363 µm). The capillaries 21a-21c can therefore be easily inserted into the bores 24a-24c.

For connection to the apparatus, the guiding elements 23 are clamped when the capillaries 21a-21c are inserted, wherein the guiding elements 23 are compressed in a radial direction along an annular ring (or a cylindrical jacket area). This may be effected e.g. in a distributor element. The inner walls of the bores 24a-24c thereby abut the outer walls of the capillaries 21a-21c in a liquid-tight fashion. The capillaries 21a-21c themselves are sufficiently stiff to prevent them from being compressed.

The illustrated polycapillary area 9 may also be called multi-lumen capillary. The multi-lumen capillary can extend over large distances, in particular, more than 1 m, wherein liquid sample in the multi-lumen capillary is only minimally mixed (and diluted) with advancing and trailing transport solvent.

Figure 3A:
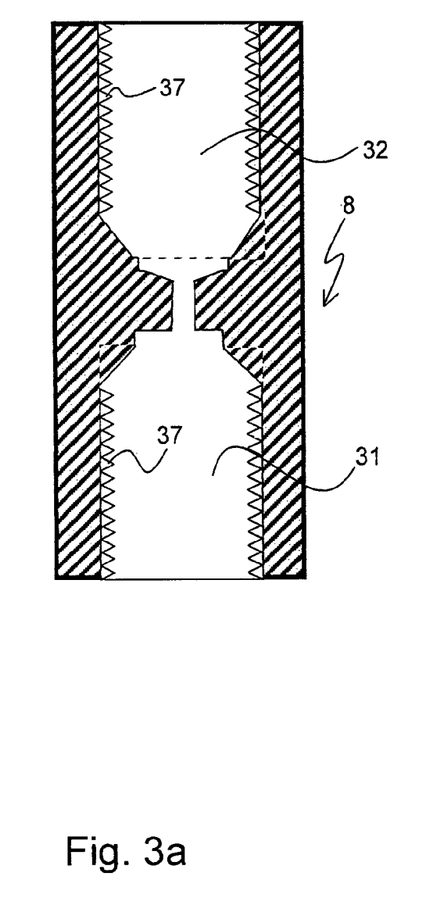
FIG. 3a shows a schematic side view of the distributor element for the invention.
Figure 3B:
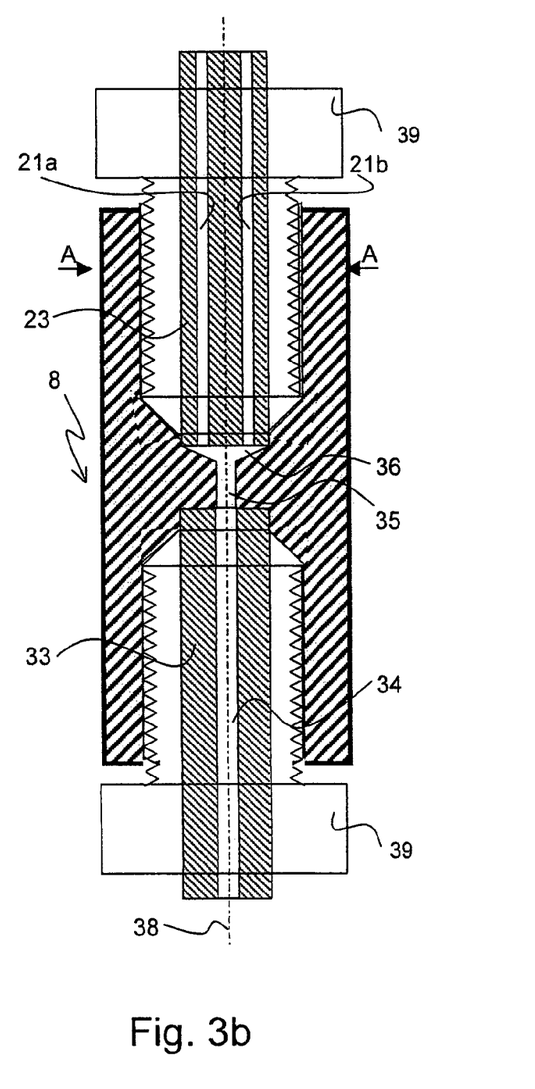
FIG. 3b shows the distributor element of FIG. 3a with clamped guiding element and capillaries.
Figure 4A:
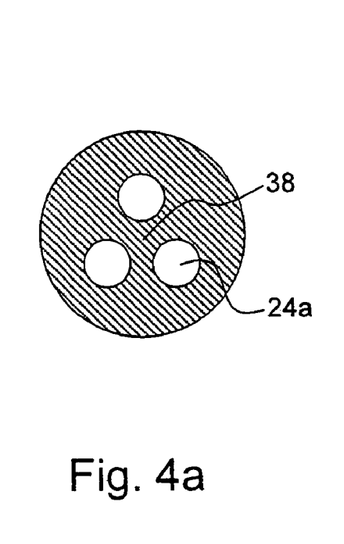
FIGS. 4a-4e show schematic cross-sectional views through guiding elements for the invention.
Figure 4B:
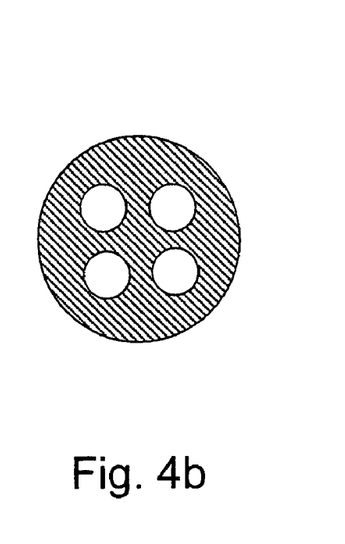
Figure 4C:
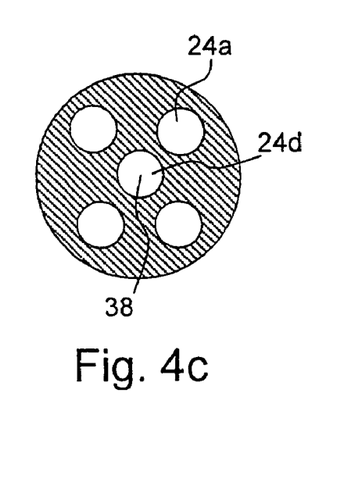
Figure 4D:
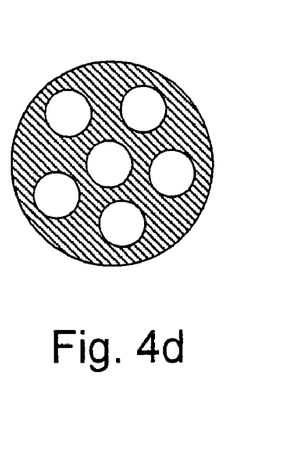
Figure 4E:
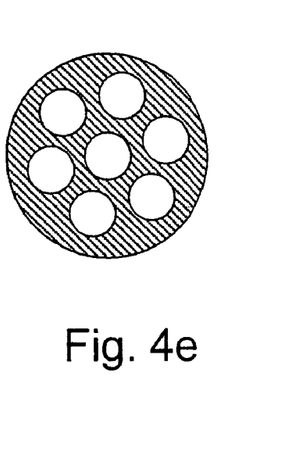

FIGS. 3a and 3b show schematic lateral cross-sections through a distributor element 8, on its own (FIG. 3a), and with clamped capillaries 21a, 21b, 34, guiding element 23, and holding element 33 (FIG. 3b).

A first recess 31 is provided for first fitting 39 of the holding element 33 to one individual, large capillary 34. A second recess 32 is provided for second fitting 39 of the guiding element 23 to the capillaries 21a, 21b of the polycapillary area. The holding element 33 and guiding element 23 are fixed through clamps thereby utilizing the elastic properties of the holding element 33 and the guiding element 23. Towards this end, a connecting technique, which has proven to be useful in chromatography, i.e. fitting 39, is used which is screwed into the distributor element 8 using a thread 37. The conical extension of the fitting 39 at its front area and the conical inner profile of the distributor element 8 produce a clamping effect (i.e. narrowing of the fitting 39 and also narrowing of the guiding element 23 or the holding element 33) which seals the capillaries 21a, 21b and 34 and keeps them in position.

A connecting bore 35 and a funnel-shaped distributor chamber 36 are provided in the distributor element 8, through which liquid can be guided from the large capillary 34 to the capillaries 21a, 21b of the polycapillary area (or vice versa). In the clamped state, the large capillary 34 and the connecting bore 35 are disposed centrally on a central axis 38 of the distributor element 8. The capillaries 21a, 21b of the polycapillary area are grouped symmetrically about the central axis 38 such that the flow paths from the opening of the connecting bore 35 to the opening of each capillary 21a, 21b in the distributor chamber 36 have the same length. In the illustrated embodiment, there is, in particular, no capillary on the central axis 38.

When the dimensions of the distributor chamber are sufficiently small compared to the lengths of the capillaries 21a, 21b, a symmetrical arrangement of the capillary openings in the distributor chamber 36 can be omitted without producing noticeable running time differences between the capillaries of the polycapillary area.

PEEK has proven to be useful as distributor element 8 material.

FIGS. 4a to 4e show some guiding elements which can be used in a recess in a distributor element (see FIG. 3a, FIG. 3b) in accordance with the invention, in a cross-section along the plane A of FIG. 3b. They show examples with three (FIG. 4a) to seven (FIG. 4e) bores 24a, 24d for capillaries.

All bores 24a, 24d are disposed symmetrically relative to a central axis 38 in order to obtain uniformly good sealing of all capillaries for radial clamping. The embodiments of FIGS. 4a, 4b only have bores 24a having identical separations from the central axis 38, which guarantees a very uniform flow distribution to the capillaries. In contrast thereto, the embodiments of FIGS. 4c-4e each also have a bore 24d on the central axis 38 (with a separation "zero" from the central axis). This increases the overall flow. When the polycapillary areas are sufficiently long (e.g. 1 m or more), a running path difference in the distributor element (of e.g. 500 µm) compared to other running path differences among the capillaries of a polycapillary area (e.g. due to production tolerances in the inner diameter) can be neglected.

Figure 5A:
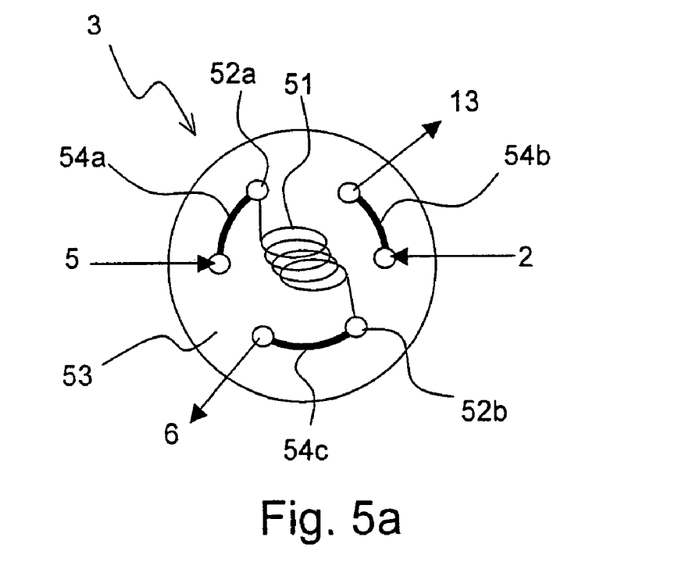
FIG. 5a shows a schematic view of a feed means for the invention in a valve position for filling a sample buffer.
Figure 5B:
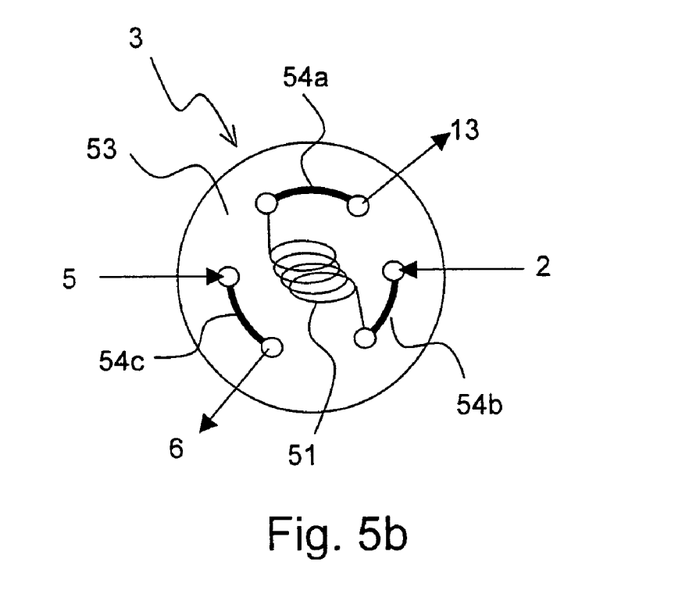
FIG. 5b shows the feed means of FIG. 5a in a valve position for feeding sample from the sample buffer into the conduit to the detector.

FIGS. 5a and 5b show the function of a feed means 3 which can be used in connection with the invention. The feed means 3 has a total of four connections to the outside:

a feed line from the pump 2 for introducing transport solvent;

a discharge line via the conduit to the detector 13;

the injection connection 5 via which liquid sample can be filled into the sample storage 51; and a discharge line to a waste container 6.

The sample storage 51 moreover has two access openings 52a, 52b.

The feed means 3 has a disc-shaped rotary valve 53 with three connecting channels 54a, 54b, 54c which can connect neighboring connections 2, 13, 52b, 6, 5, 52a to each other.

In the position of the rotary valve 53 of FIG. 5a, liquid sample can be filled from the injection connection 5 via the connecting channel 54a and the opening 52a into the sample storage 51. The sample storage 51 is designed as a spiral capillary. Excessive liquid sample flows through the opening 52b and the connecting channel 54c into the waste container 6. At the same time, transport solvent is guided from the pump 2 via the connecting channel 54b to the detector 13.

In the position of the rotary valve 53 of FIG. 5b, the sample is fed into the system. The rotary valve 53 was turned to the right through 60° (clockwise direction) as compared to FIG. 5a. Transport solvent is guided from the pump 2 via the connecting channel 54b into the sample storage 51. The liquid sample previously introduced into the sample storage 51 is forced out via the connecting channel 54a and to the detector 13.

Figure 6A:
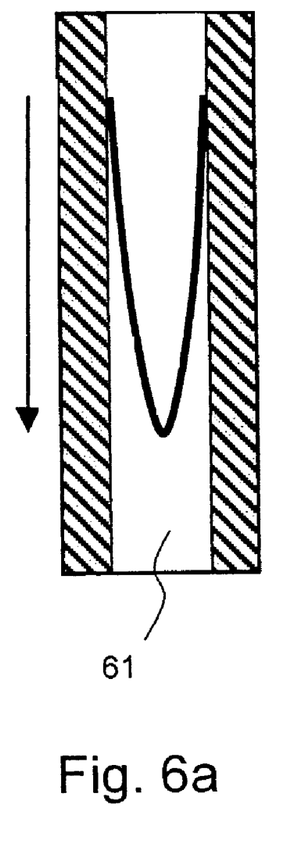
FIG. 6a shows a schematic view of a flow profile of a large capillary.
Figure 6B:
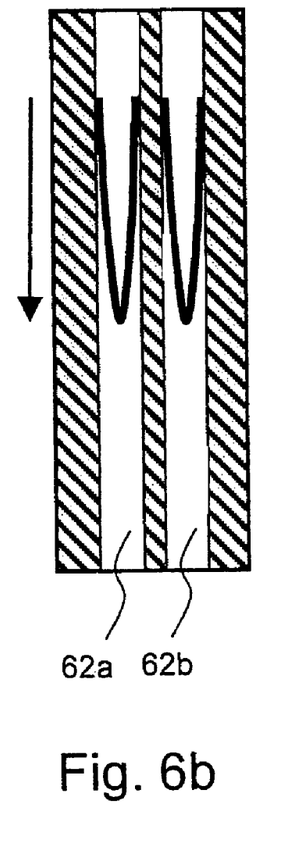
Figure 6C:
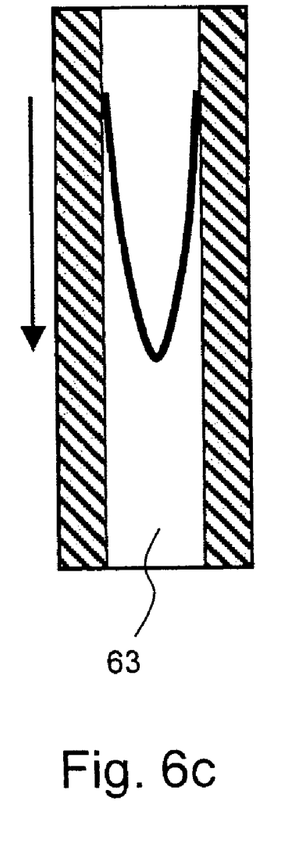
FIG. 6c shows a schematic view of the flow profile of a capillary with the same diameter as the capillary of FIG. 6a but with hydrophobic inner coating.

FIGS. 6a through 6c show smearing of liquid samples during movement in the capillaries under different conditions. FIG. 6a represents a capillary 61 of a typical size, FIG. 6b shows two small capillaries 62a, 62b whose overall cross-sectional area corresponds to the cross-sectional area of the large capillary 61 of FIG. 6a, and FIG. 6c shows a large capillary 63 like in FIG. 6a but with a hydrophobic inner surface (e.g. due to coating).

A thin, disc-shaped sample (e.g. produced by NMR excitation in only one disc-shaped area in the capillary) is pushed through each capillary by following transport solvent, in FIGS. 6a through 6c from the top to the bottom. In FIGS. 6a, 6b, 6c, the same amounts of solvent volume were added over the same time period and uniformly distributed to the two parallel capillaries 62a, 62b (FIG. 6b).

In most cases smearing of the sample can observed. The liquid sample attains an approximately parabolic profile. In the center of the capillary, the sample advances more quickly and the sample advances more slowly at the capillary edge.

Maximum smearing takes place in the uncoated large capillary 61 of FIG. 6a. The smearing can be reduced through using a hydrophobic inner coating (see FIG. 6c) and also through distribution of the liquid transport to several (in the present case two) capillaries 62a, 62b in accordance with the invention.

The following table shows quantitative values for the smearing degree in an individual capillary and a double capillary (dual lumen capillary) which were determined through experiments. The position of the tip of the sample front is thereby compared to the position of a flat sample line with a hypothetic absolutely non-smeared sample ("plug flow") with a certain amount of added solvent.

|  | Inner diameter in mm | Volume in μl/mm | Smearing in % |
| --- | --- | --- | --- |
| Individual capillary (FEP) | 0.512 | 0.206 | 154.5 |
| Double capillary (FEP) | 0.363 | 2 × 0.104 | 111.4 |

By using two smaller capillaries of each 0.363 μm instead of one single large capillary of a diameter of 512 μm, smearing can be considerably reduced (by approximately 43%) with the same overall cross-sectional area which is available for the flow.

In summary, the invention describes a measuring apparatus for investigating liquid samples, wherein the liquid samples are transported via a conduit from a feed means to a measuring location. The conduit is thereby largely designed as a polycapillary area in which several capillaries take over parallel transport of liquid sample and transport solvent. The individual capillaries are designed such that liquid sample flows through them within the same time.

In the simplest case, the capillaries are of identical design, so that all capillaries have the same flow velocity and also identical lengths. The several individual capillaries can have a smaller inner diameter than one single capillary of the same overall cross-sectional area. This reduces spreading of liquid sample. The higher sample concentration after transfer to the measuring location improves the SNR of the analysis.

I claim:

1. An apparatus for analyzing a measuring substance dissolved in a solvent, the apparatus comprising:
   a feed means;
   means defining a measuring location; and
   a conduit for transporting the dissolved measuring substance from said feed means to said measuring location, said feed means optionally feeding a solvent or a dissolved measuring substance into said conduit, said conduit having a polycapillary area with N parallel, connected capillaries, wherein individual capillaries thereof have identical flow times from said feed means to said measuring location, with $N \geq 2$.

2. The apparatus of claim 1, wherein said individual capillaries have identical inner diameters and identical lengths.

3. The apparatus of claim 1, wherein lengths of individual capillaries are adjusted to compensate for different flow speeds in said individual capillaries, thereby ensuring substantially equal flow times through all said individual capillaries.

4. The apparatus of claim 1, wherein said conduit comprises a chromatography column.

5. The apparatus of claim 1, wherein said conduit feeds into a measuring cell at said measuring location.

6. The apparatus of claim 1, wherein said measuring location comprises a polycapillary area.

7. The apparatus of claim 1, wherein said capillaries have a hydrophobic inner coating.

8. The apparatus of claim 1, wherein a number N of capillaries in said polycapillary area is between 2 and 7.

9. The apparatus of claim 1, wherein an inner diameter of said capillaries is between 50 μm and 500 μm.

10. The apparatus of claim 1, further comprising a plastic jacket in which the capillaries extend.

11. The apparatus of claim 1, wherein said capillaries are individually guided, in some areas, through bores of guiding elements.

12. The apparatus of claim 1, wherein the apparatus is designed as an NMR spectrometer or UV detecting apparatus.

13. The apparatus of claim 1, wherein a distributor element for said N capillaries is disposed at an entry to said polycapillary area.

14. The apparatus of claim 13, wherein said N capillaries in said distributor element are disposed symmetrically about a central axis and have identical separations from that central axis.

* * * * *